United States Patent [19]

Lavigna et al.

[11] 4,134,785
[45] Jan. 16, 1979

[54] REAL-TIME ANALYSIS AND CONTROL OF MELT-CHEMISTRY IN CRYSTAL GROWING OPERATIONS

[75] Inventors: Robert J. Lavigna, Bath; Charles W. Pearce, Allentown; Raymond E. Reusser, Bethlehem, all of Pa.

[73] Assignee: Western Electric Company, Inc., New York, N.Y.

[21] Appl. No.: 787,135

[22] Filed: Apr. 13, 1977

[51] Int. Cl.$^2$ .............................................. B01J 17/18
[52] U.S. Cl. .................................... 156/601; 422/245; 422/249
[58] Field of Search ................. 156/601, 617 SP, 618; 23/273 SP, 301; 73/425.6

[56] References Cited

U.S. PATENT DOCUMENTS

| | | | |
|---|---|---|---|
| 3,103,627 | 9/1963 | Schneider | 324/58.5 |
| 3,354,723 | 11/1967 | Smith | 73/425.6 |
| 3,582,778 | 6/1971 | Faukner | 331/107 |
| 3,859,857 | 1/1975 | Falk | 73/425.4 R |
| 3,905,238 | 9/1975 | Falk | 73/425.6 |

FOREIGN PATENT DOCUMENTS 1352567   5/1974   United Kingdom ..................... 156/601

OTHER PUBLICATIONS

IEEE Trans. on Instrumentation and Measurement 12/64 Bichara et al. pp. 323-328.
Proc. of the IRE, 5/61, Jacobs et al., pp. 928-932.
1962 IRE Cov., Jacobs et al., pp. 30-42.
Journal of Physics E Scientific Instruments, 12/72, Nancollas et al., pp. 1186-1189.

*Primary Examiner*—Hiram H. Bernstein
*Attorney, Agent, or Firm*—George W. Houseweart; Robert Y. Peters

[57] ABSTRACT

To improve the control over resistivity of grown single crystalline ingots, to reduce the turn-around time between growth of successive ingots in a particular crystal grower and to enable recycling of otherwise junk material, a sample of a molten material (the "melt") from which the ingot is to be grown is withdrawn from the crystal grower, cooled, and analyzed. Based on the analysis, controlled additional amounts of the material and/or a dopant impurity are added directly to the melt to restore it to a desired chemical composition. Thus, avoidable is costly and time-consuming cooling of the melt and restarting the system with a completely new charge of material and impurity, and achievable is uniformity of resistivity among the successively grown ingots. Preferably the sample is withdrawn from the melt into a quartz tube which is inserted into the system through a port. The sample is rapidly cooled and solidified and inserted into a waveguide system where a microwave absorption measurement provides a number which is readily converted into resistivity of the sample, and then, into doping level of the melt.

8 Claims, 6 Drawing Figures

REAL-TIME ANALYSIS AND CONTROL OF MELT-CHEMISTRY IN CRYSTAL GROWING OPERATIONS

BACKGROUND OF THE INVENTION

Field of the Invention

This invention relates to methods of, and apparatus for, growing crystalline material; and more particularly, to a method affording real-time analysis and control of melt-chemistry in crystal growing operations.

It is conventional to grow a single-crystalline ingot from a polycrystalline material by preparing a melt of such material and contacting the surface of the melt with a previously prepared seed crystal of the same material but with the desired crystalline lattice orientation. In growing the single crystalline ingot, the seed crystal is withdrawn from the melt at a rate of the order of a few inches per hour while the seed crystal (and hence the ingot), is counter-rotated with respect to the melt. With this technique, single crystalline ingots several feed in length and several inches in diameter are routinely grown, particularly in the silicon semiconductor industry.

In this industry, it is conventional to dope the melt with either an N-type dopant impurity, such as phosphorus, antimony, or arsenic, and/or a P-type dopant impurity, such as boron, aluminum and gallium.

A serious problem facing this industry is the difficulty of controlling the dopant concentration of the melt and the ultimately grown single crystalline ingot, and hence the resistivity of such ingot. There are many reasons why it is desirable to control the resistivity of the grown crystalline ingot. For example, control of resistivity is required for the preparation of electrically isolated portions of wafers which have been cut from the ingot in the manufacture of integrated circuits. Also, since resistivity has a bearing on the depth to which dopant impurities may be diffused and a bearing on the concentration gradient of diffused dopant impurities, it is necessary to control resistivity. Often the manufacture of certain semiconductor devices requires the control of resistivity of wafers used in making the devices to within narrow, and difficult to achieve, ranges.

One reason for the difficulty of controlling resistivity is that while growing a crystalline ingot from a melt, the chemistry of the melt (i.e., the concentration of dopant impurity with respect to the basic material, for example silicon) does not remain constant as the growing operation, which may require many hours, proceeds. Rather, the dopant impurity tends to evaporate from the melt at a rate depending in complex ways upon temperature, temperature gradients, geometry, concentration, and vapor pressure in the crystal growing apparatus.

Another reason for the difficulty of controlling the resistivity is segregation effects, whereby the concentration of the dopant impurity which becomes a part of the grown crystalline ingot is not the same as the concentration of the dopant impurity in the melt itself. More specifically, the concentration of the dopant impurity is usually less in the grown crystalline ingot than in the melt. As a result, the dopant concentration within the ingot itself increases with longitudinal position in a complex way which is not readily predictable precisely from prior empirical results.

The evaporation and segregation effects previously mentioned are particularly troublesome for melts which have been recharged several times. This recharging involves growing a single crystalline ingot of less than full length and width from a polycrystalline melt, adding new polycrystalline material to the melt, melting such material, and continuing to grow the single crystalline ingot.

Moreover, it is advantageous to reconstitute a melt after a crystalline ingot has been grown by adding more polycrystalline material. Thus, avoidable is the costly and time-consuming process of cooling the remaining melt and completely restarting the system with a new charge of polycrystalline material and dopant impurity, and achievable is uniformity of resistivity among the successively grown ingots. From this aspect, it is desirable in general to analyze a melt from which a crystalline ingot has been grown, or while a crystalline ingot is being grown, and to recharge that melt with a proper amount of polycrystalline material and/or dopant impurity so that second and successive crystalline ingots can be grown without cooling down the system with a consequent substantial saving in electrical energy, polycrystalline material and crucibles for the melt.

It is highly advantageous for ecological and economic reasons to recycle various portions of grown crystalline ingots which are not suitable for other uses for whatever reasons. Such portions may include the ends of grown crystalline ingots, as well as junk which may be broken or otherwise deleteriously affected in subsequent processing. Because such material, which may be referred to as primary material, has various concentrations of dopant impurities, it is difficult to control the resistivity of the grown crystalline ingot. Using real-time analysis and control of melt-chemistry in a crystal growing operation, a quantity of material of undetermined chemistry can be melted, analyzed, and, by adding amounts of primary material and/or dopant impurity, the melt-chemistry can be adjusted to a desired composition known to be suitable for growing a crystalline ingot of a predetermined desired resistivity.

Still another reason for the difficulty of controlling the resistivity of the grown crystalline ingot are the random sources of dopant and other impurities that increase the impurities beyond the desired amount. Such impurities are phosphorus and/or boron which are often contained in the primary material or the crucible for holding the melt.

SUMMARY OF THE INVENTION

In view of the aforementioned and other problems inherent in conventional methods and apparatus for growing crystalline material, it is an object of this invention to provide new and improved methods and apparatus to enable real-time analysis and control of melt-chemistry in crystal growing processes.

The aforementioned and other objects are achieved in accordance with this invention by withdrawing a sample from the melt, cooling and analyzing the sample. Based on the analysis, controlled additional amounts of primary material and/or dopant impurity are added directly to the melt to establish a known desired chemical composition avoiding the need for cooling of the old melt and restarting the system with a completely new charge of primary material and dopant impurity.

In accordance with one presently preferred embodiment of the invention, a melt is sampled by inserting a small diameter tube into the system through a port, and withdrawing a sample of the melt into the tube. The sample is rapidly cooled and solidified (or frozen) thus producing a polycrystalline sample, which is then inserted into a waveguide. a microwave absorption measurement in the waveguide provides a number which is readily converted into resistivity of the sample and then into doping level of the melt.

Once the doping level of the melt is known, the amount of primary material and/or dopant material needed to establish the melt at a desired quantity and doping level can be readily determined and added to the system.

Advantageously, the sample tube is of quartz material such that the polycrystalline sample therein can be inserted into the waveguide while still encased in the quartz. The quartz sampler preferably is of a particular configuration, so that the polycrystalline material drawn thereinto is of a known configuration and volume, thus facilitating repeatable microwave measurements without recalibration. The quartz is also advantageous in that it reduces the amount of reflection of the microwave power from the sample, in accordance with principles used in optics to produce anti-reflection coatings by building up layers of varying indices of refraction.

BRIEF DESCRIPTION OF THE DRAWING

The aforementioned and other features, characteristics and advantages and the invention in general will be better understood from the following more detailed description taken in conjunction with the accompanying drawing in which.

Figure 1:
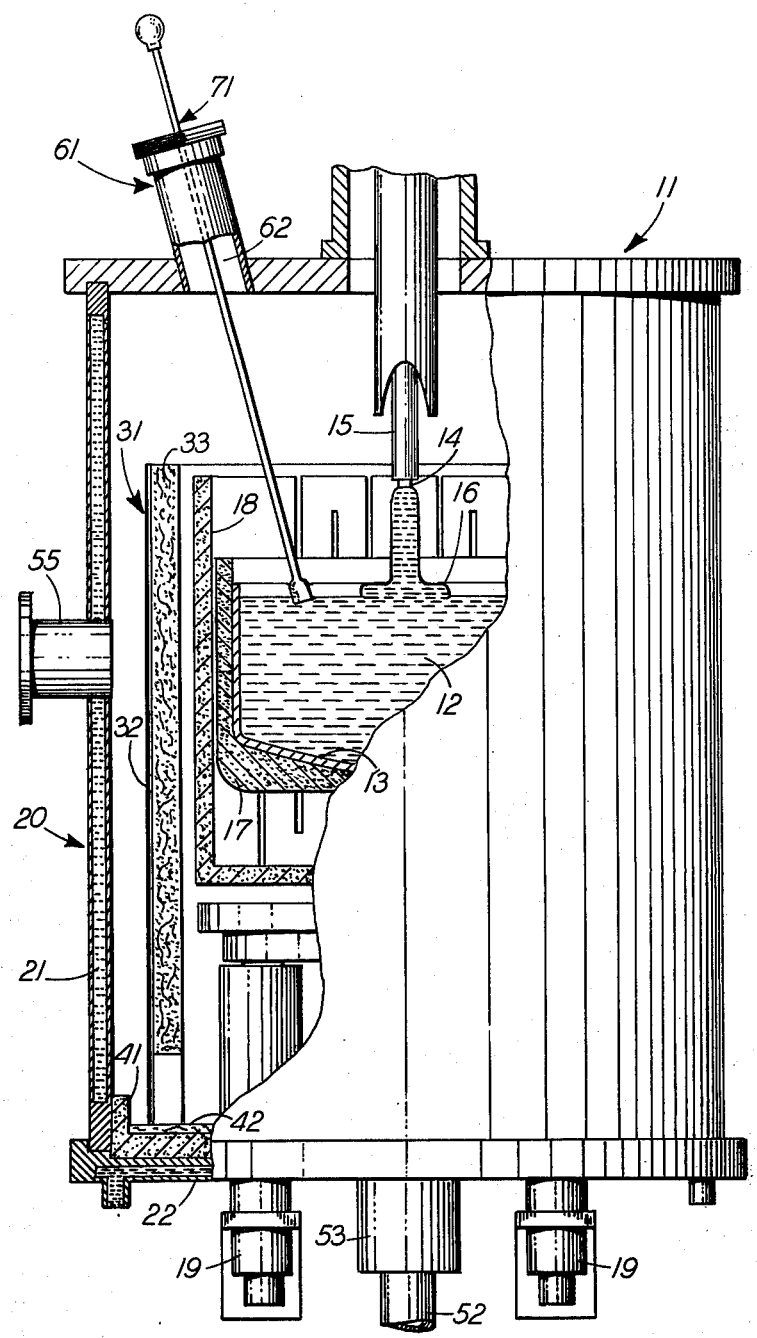
FIG. 1 is a partially broken-away, cross-sectional view of a crystal grower, illustrating a technique for withdrawing a sample from a melt.

Throughout the figures, reference numerals are repeated to indicate corresponding features where appropriate; and it will be appreciated that the figures are not necessarily drawn to scale.

DETAILED DESCRIPTION

For simplicity and clarity of explanation, the invention will be described hereinafter principally in connection with a Czochralski-type crystal grower adapted for producing a single crystalline silicon ingot from a polycrystalline silicon melt which may, but need not be, doped with an impurity for determining the conductivity type and resistivity of the grown crystalline ingot. However, it is to be understood that the described real-time sampling analysis and control techniques in accordance with this invention may well be used with other apparatus for producing other solid crystalline material and the control of other impurities.

With reference now to FIG. 1, there is illustrated in a frontal, cross-sectional, partially broken-away view a Czochralski-type crystal grower, designated generally by the numeral 11. As in typical Czochralski-type crystal growers, material 12 from which a crystalline ingot is to be grown is held in a molten state within a heated crucible 13. A seed crystal 14 is held in the end of a seed shaft 15. The free end of the seed crystal 14 is touched to the surface of the molten material 12, while the crucible 13 and the seed shaft 15 are counter-rotated, i.e., in opposite directions.

After the seed crystal 14 is touched to the surface of the molten material 12 under temperature and other conditions known to those skilled in the art, the molten material solidifies on the seed crystal with the same lattice orientation as the seed crystal. By slowly withdrawing the seed crystal, typically at the rate of the order of a few inches an hour, and rotating the seed shaft 15, a single crystalline ingot 16 is grown from the molten material 12.

Operation of at least one type of Czochralski crystal grower is described in U.S. Pat. No. 3,679,370 issued July 25, 1972, to J. J. Czeck et al., and further details of operation may be found in U.S. Pat. No. 3,698,872 issued Oct. 17, 1972, to R. E. Reusser, both patents being assigned to the assignee hereof.

In FIG. 1 the crucible 13, which is typically formed of quartz where the molten material 12 is of silicon, is surrounded and supported by a black body housing 17. The housing 17 typically is formed of graphite and in the art is typically referred to as a "susceptor" for historical reasons. In early crystal growers, heating was provided primarily by radio frequency heating, and the housing 17 operated as a susceptor to convert the radio frequency energy into thermal energy. However, with the use of larger masses of molten material, radio frequency heating was supplanted with thermal resistance, radiative-type heating.

Such thermal resistance heating is contemplated for the crystal grower 11 of FIG. 1 and is illustrated generally as element 18, which is a resistance-type heater connected to a source of electrical power (not shown) through water-cooled electrodes 19. The crucible 13, the susceptor 17 and the heating element 18 are all contained within an insulated chamber designated generally by the numeral 20. The chamber 20 is provided with fluid-cooled metallic sidewalls 21 and a fluid-cooled metallic bottom plate 22. An insulating member, designated generally by the numeral 31, is located within the chamber 20. The member includes a metllic support element 32 and an insulating element 33, advantageously of graphite felt. The bottom plate 22 is covered by a cup-shaped member 41 of solid graphite. Overlying the member 41 is a layer 42 of graphite felt for providing protection against breakout of the molten material 12 in the event that the crucible 13 should rupture, all of which is described in greater detail in the above-referenced R. E. Reusser U.S. Pat. No. 3,698,872.

A shaft 52 is coupled through seals 53 to provide a means for rotating and vertically moving the crucible 13 and the susceptor 17 theresurrounding. It should also be noted that chamber 20 is provided with a large vacuum port 55 through which roughing vacuum can be provided to the chamber 20 prior to introduction of a positive pressure atmosphere of an inert gas, such as argon, in which the crystalline ingot 16 typically is grown in accordance with the Czochralski technique.

With reference now to the upper portion of FIG. 1, there is shown a viewing port, designated generally 61, coupled by a passageway 62 into the top of the crystal grower 11. Port 61 typically includes a transparent plate at the opening thereof, through which the crystal growing operation can be viewed while in process. The port 61 is typically 3 to 5 inches in diameter and provides one convenient means by which a sampler, designated generally 71, can be inserted into the crystal grower 11. It is recognized that alternate access port designs may be advantageously employed to minimize the disturbance to a growing crystal during real-time sampling. Such insertion without introducing undue contaminants is facilitated by the above-mentioned fact that during the crystal growing operation, the internal portion of the crystal grower 11 is under a positive pressure of an inert gas such as argon.

Figure 2:
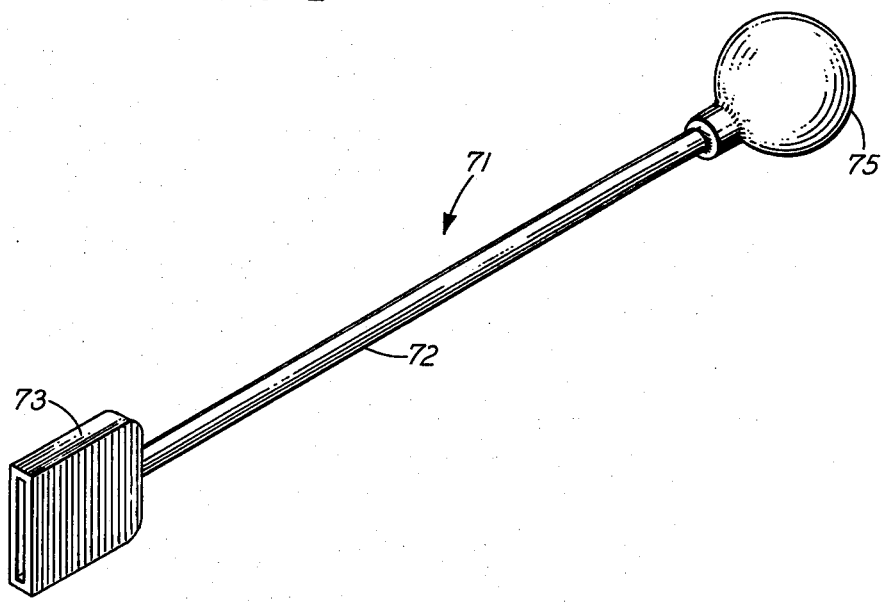
FIG. 2 is a pictorial view of a sampler suitable for use in accordance with one embodiment of this invention.

The structure of sampler 71 can be seen in more detail in FIG. 2, which is a pictorial view. As seen, sampler 71 includes a hollow, tubular portion 72 communicating with a hollow, rectangular portion 73. A flexible hollow ball portion 75 is attached to one end of tubular portion 72. Portions 72 and 73 advantageously are formed from a solid refractory material capable of withstanding the high temperatures, in the order of about 1400° C to about 1500° C, that occur in the crystal grower 11 without contaminating the grower or its materials. Quartz is a particularly advantageous material for use because it is relatively inert and lossless at microwave frequencies; however, this material must be quickly inserted and withdrawn from the melt to minimize shape distortion. Because of this lossless property of the sampler at microwave frequencies, a sample withdrawn and cooled in sampler 71 can be inserted directly into a waveguide for microwave absorption measurements without removal from the sampler, a distinct advantage which will be discussed in detail hereinbelow.

To withdraw a sample from crystal grower 11, sampler 71 is inserted through port 61, as shown in FIG. 1, sufficiently to immerse the rectangular portion 73 thereof into the molten material 12. By squeezing the flexible ball portion 75 before the sampler is immersed into the material, a partial vacuum is created in the sampler 71, and this enables some of the molten material 12 to be withdrawn into the sampler by releasing the pressure from the ball portion 75.

Once some of the molten material 12 has been withdrawn from the crystal grower, the sampler 71 is removed from the port 61 and a cover is replaced over the port 61 to avoid entrance of undesired contaminates thereinto. The molten material in the removed sampler 71 is rapidly cooled, for example, within a few seconds, in air or by other suitable cooling means or media to solidify the material in the sampler 71.

Relatively rapid solidification is desirable to prevent the dopant impurities in the polycrystalline sample from migrating to grain boundaries during the cooling process. If such migration to grain boundaries were allowed, subsequent microwave analysis would detect only those impurities which has not migrated to grain boundaries and would thus provide less accurate results.

Also, if the sample is withdrawn too slowly, segregation effects may result and the concentration in the sample would not represent that of the melt.

Figure 3:
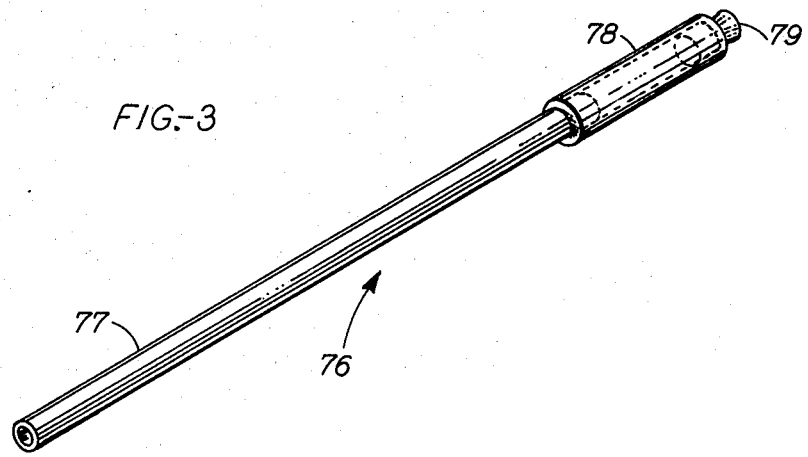
FIG. 3 is a pictorial view of another sampler suitable for use in accordance with one embodiment of this invention.
Figure 4:
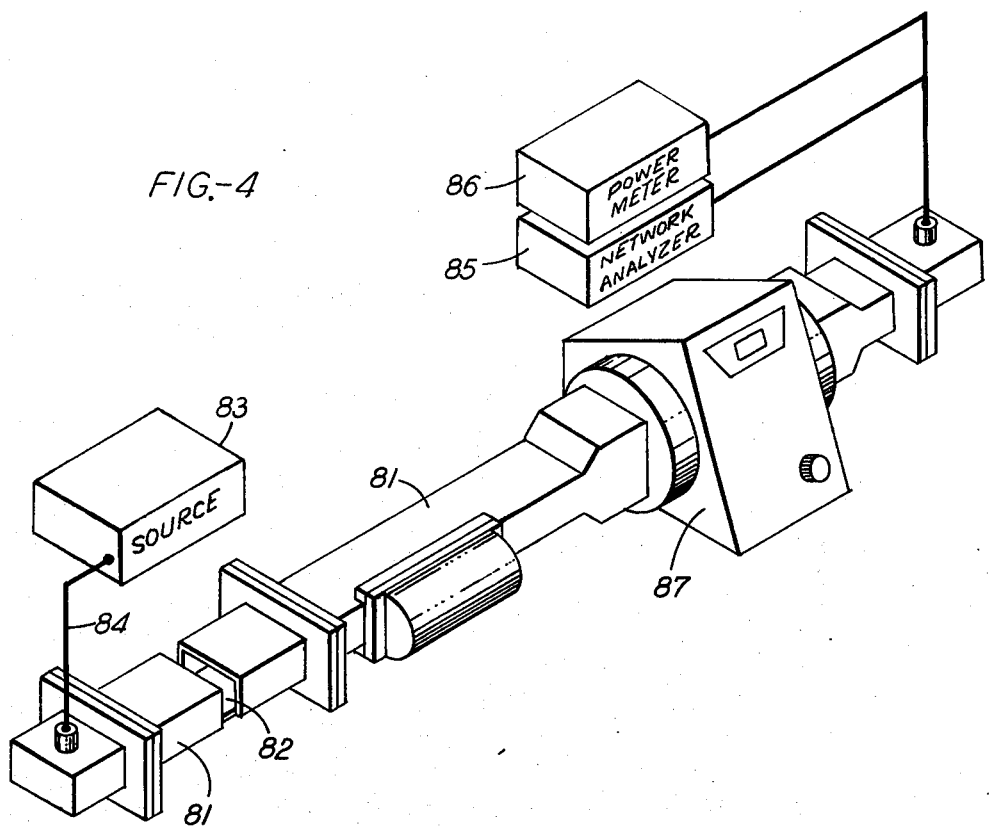
FIG. 4 illustrates a waveguide and suitable associated electronic apparatus, partially in schematic, for performing microwave absorption measurements in accordance with one embodiment of this invention.

In FIG. 3, there is shown an alternate form of a sampler suitable for use in accordance with this invention. As seen in FIG. 4, the sampler 76 includes a hollow, tubular portion 77, again advantageously of quartz, and a section of flexible tubing 78 slipped relatively tightly around one end of tubular portion 78. A plug 79 is inserted in the end of flexible tubing 78 to create an airtight seal, so that by squeezing portion 78, air may be expelled from quartz tubular portion 77 to enable drawing a sample thereinto by a partial vacuum.

With reference to FIG. 4, there is shown partially schematically and in block diagram form a waveguide system including suitable associated electronic apparatus for performing microwave absorption measurements in accordance with one embodiment of this invention. As seen, a waveguide 81 of the system is of generally rectangular configuration, with the size of the rectangle being larger than the rectangular portion 73 (FIG. 2) of the sample 71. That rectangular portion 73 of sampler 71 is inserted into a slot 82 in waveguide 81 for performing the microwave absorption measurement. For that measurement, microwave power of a predetermined magnitude and frequency is provided by a source 83 through a coaxial coupling 84 to one end of the waveguide 81. A network analyzer 85 and a power meter 86 are coupled coaxially to the other end of waveguide 81. Either or both the analyzer and meter may be used to determine the amount of microwave power transmitted from the source 83 and through a sample which may be in the slot 82.

In operation, with a sample of polycrystalline material encased in the portion 73 of the sampler 71 located in the slot 82, power is supplied from the source 83, transmitted through the waveguide 81, and through the sample to the network analyzer 85 and the power meter 86. A reading is taken from either the network analyzer 85 or the power meter 86 to determine the magnitude of the transmitted power. Thereafter, the sample is withdrawn from the slot 82 and the same magnitude of power is transmitted from the source 83 into the waveguide 81 and is acted upon by a calibrated variable attenuator 87, which is adjusted while observing the power meter 86 to produce the same attenuation, and thus to enable transmitting of the same magnitude of power to the meter 86 as was transmitted by the sample previously. In this manner, with the calibrated attenuator, one can readily determine the amount of attenuation which was previously produced by the sample.

Figure 5:
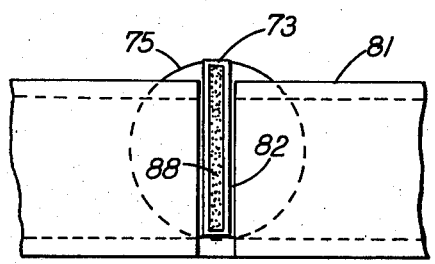
FIG. 5 is a cross-sectional view showing a sample in a waveguide.

In FIG. 5 there is illustrated in side view a sample 88 encased in the quartz rectangular portion 73 in the slot 82 in the waveguide 81. As seen the slot 82 is adapted in size to be just sufficient to receive the portion 73 without an undue degree of looseness of fit.

As will be appreciated, the amount of attenuation caused by sample 88 will depend upon its geometry, thickness, volume, and other physical parameters. As such, for repeatable measurements without recalibration, a sample of known and repeatable geometry must be obtained for measurement. It is for this reason that the rectangular sample is taken in the sampler 71 shown in FIG. 2 so that the sample is always of the same geometry. A sample of the type obtainable in the sampler 71 in FIG. 2 is preferred because it can be inserted as shown in FIG. 5 into the rectangular waveguide 81 so as to cover the entire transmitting section, i.e., interior, cross-sectional area of the waveguide 81, and thus cause a greater degree of attenuation than would a test sample of the type obtainable in a sampler such as shown in FIG. 3. This of course is because attenuation is on a per unit volume basis and a greater degree of volume is exposed to the transmitting microwave with the sample 88.

Figure 6:
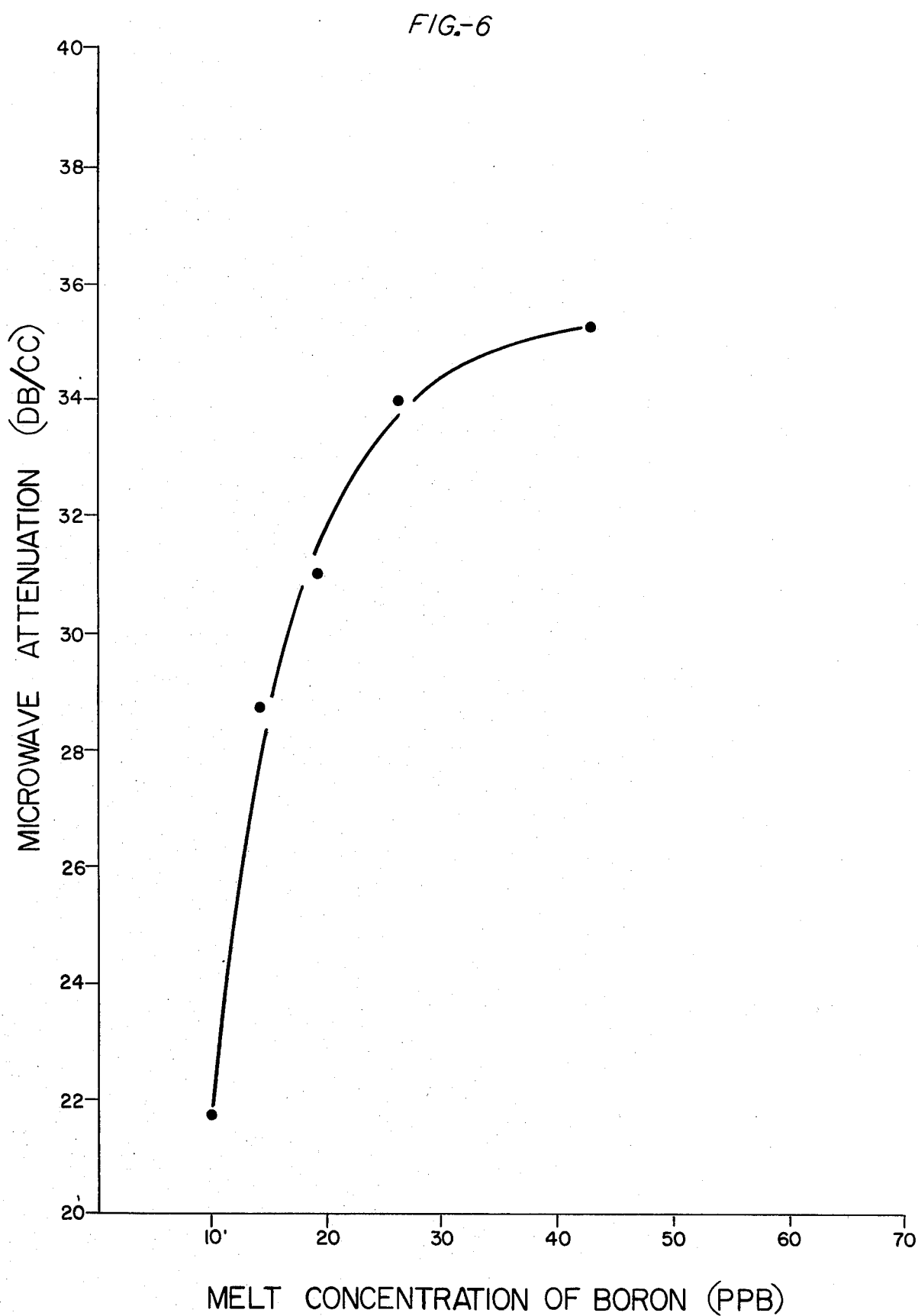
FIG. 6 illustrates a calibration diagram for relating microwave attenuation with concentration of dopant impurity in a melt.

With reference now to FIG. 6, there is shown a calibration diagram in which attenuation caused by the sample is shown on the vertical axis and the corresponding concentration of dopant impurities in a melt is shown on the horizontal axis.

Data for such a diagram can be obtained by sampling melts of known chemistry and them performing microwave absorption (attenuation) analysis measurements on these samples. Alternatively, of course, such data can be theoretically calculated and/or empirically derived by other means which will be apparent to those in the art.

More specifically and by way of an example, a melt of polycrystalline silicon was doped to a boron concentration of 65 parts per billion, ppb. Then a sample was withdrawn in the sampler 76 of FIG. 3, which has an inside diameter of to 0.188 inch. Then, undoped polycrystalline silicon was added to the melt reducing the concentration to 45 ppb and again a sample was withdrawn. The dilution process was continued until a melt concentration of 10 ppb was obtained. The calculated melt concentration based on dilution assumes no evaporation of boron from the melt or residual boron in the undoped polycrystalline silicon.

As seen from FIG. 6, the microwave absorption of the polycrystalline silicon sample withdrawn from the melt at each dilution does vary as a function of melt concentration. This means the microwave absorption of such a sample can be used to control and/or determine melt chemistry.

Similar curves are obtainable for arsenic doped melts and different sample geometries. The flattening out of the curve above 40 ppb is due to the "skin effect" of the microwave measurements and for most applications the sampler 71 of FIG. 2 eliminates this effect.

With reference now to the microwave absorption measurements, it is known that the amount of reflection a traveling microwave experiences encountering a medium of different indices of refraction is an easily calculated quantity. For example, at a wave length of 2.5 microns relative to air, 30% of an incident electromagnetic wave will be reflected from a silicon surface where the silicon has an index of refraction equal to 3.42. As is also well known, it is possible to reduce the amount of reflection by coating the surface with a material having an intermediate index of refraction. Silicon dioxide or quartz having an index of refraction of 1.42 is a nearly ideal intermediate layer. For this reason, the measurement of the polycrystalline silicon samples drawn from the melt while still encased in the quartz samplers is an advantageous aspect of this one embodiment of the present invention. This of course is due to the fact that more of the energy is transmitted through the sample rather than being reflected therefrom, resulting in a higher measured attenuation due to sample absorption compared to the sample's reflection. For this reason, a better and a more accurate measurement can be obtained.

At this point, it is believed that principles of this invention have been described in sufficient detail to enable one skilled in the art to practice the invention. Although the invention has been described in part by making detailed reference to a specific embodiment, such detail is intended to be and is understood to be instructive rather than restrictive. It will be appreciated by those skilled in the art that many variations may be made in the structure and in the modes of operation without departing from the spirit and scope of the invention as disclosed in the foregoing teachings.

For example, the invention need not be limited to dopant impurities. In the growing of single crystal silicon, oxygen and carbon impurities are also of interest. Excessive amounts of carbon may result in the grown crystalline ingot losing its dislocation-free state and going to a polycrystalline state. Moreover, oxygen can affect the grown ingot as it is processed into semiconductor devices and thereby reduce control of the involved processes and the ultimately produced devices.

More specifically, using the sampler 71, a sample of the polycrystalline silicon melt was taken from the crucible 13. The sample was then removed from the sampler 71 and using a conventional infrared spectrophotometer and previously published calibration curves for carbon content of single crystal silicon, a melt concentration of 17.8 ppm was measured. Adjusting the melt concentration of carbon by its well known segregation coefficient (k equals 0.07) a value of 1.3 ppm of carbon was obtained. Thus, by measuring the melt concentration for carbon, it can be determined a priori when the melt concentration is such that the level would exceed approximately 10 ppm, which is the level where single crystal perfection can be lost.

Moreover, it is apparent that the sampler 71 need not be made of quartz but may be of any suitable refractory material capable of withstanding the temperatures involved, provided, of course, that such material does not provide deleteriously contaminating impurities into the sample being withdrawn or into the melt being sampled.

Further, as allued to above, the microwave absorption measurement need not be made with the material encased in the sampler 71. Rather, the sample may be removed from the material by breaking or by other means prior to the measurement.

What is claimed is:

1. A method of controlling the resistivity of each of a plurality of single-crystalline ingots of desired size which may be successively grown from a melt which may be successively reconstituted as desired for each ingot grown, wherein the melt contains polycrystalline material and an impurity, and wherein the improvement comprises the steps of:
    maintaining at least a portion of the melt in its melted state for each ingot grown from the melt which portion of melt may be retained and reconstituted for a successive ingot after an ingot is grown;
    withdrawing a sample of the maintained melt, the composition of the melt varying as a single-crystalline ingot is grown from the melt and varying in accordance with the freezing of the melt into an ingot;
    cooling the sample to solidify it into a polycrystalline structure;
    determining an electrical characteristic of the polycrystalline sample, which characteristic is indicative of the level of the impurity of the maintained melt and which level of the impurity is indicative of the resistivity of a single-crystalline ingot grown from the melt;
    comparing the determined electrical characteristic of the sample with a value of that electrical characteristic desired in an ingot; and
    reconstituting the maintained melt according to the comparison and according to the desired size of an ingot by adding an amount of polycrystalline material or of the impurity or of both to the maintained melt to control the resistivity of each of a plurality of single-crystalline ingots grown from the melt.

2. A method as recited in claim 1, wherein the impurity is a dopant and the sample is withdrawn by suction into a hollow member to produce a sample of known configuration.

3. A method as recited in claim 1, wherein the sample is rapidly cooled to solidify the sample.

4. A method as recited in claim 1, wherein the determining step is accomplished by performing a microwave absorption measurement on the sample to produce a value of microwave absorption at a particular frequency.

5. A method as recited in claim 4, including the additional step of converting the microwave absorption value into a value representing concentration of dopant impurities in the melt.

6. A method of controlling the resistivity of each of a plurality of single-crystalline semiconductor ingots of a desired size successively grown from a melt, which melt may be successively reconstituted as desired for each ingot grown to achieve substantial uniformity of resistivity among successively grown ingots, wherein the melt contains semiconductor polycrystalline material and a dopant, and wherein the improvement comprises the steps of:
maintaining at least a portion of the melt in its melted state for each ingot grown from the melt which portion of melt may be retained and reconstituted for a successive ingot after an ingot is grown;
inserting a refractory sample into the melt, the composition of the melt varying as a single-crystalline ingot is grown from the melt and varying in accordance with the freezing of the melt into an ingot;
drawing by suction into the sampler a sample of the melt of known volume and configuration;
rapidly cooling the sampler to rapidly solidify the sample into a polycrystalline structure;
inserting the polycrystalline sample, while still contained in the sampler, into a waveguide means;
transmitting microwave power within the waveguide means and through the sample while it is still contained in the sampler;
measuring the microwave absorption of the contained sample at a predetermined microwave frequency;
comparing the measured microwave absorption of the contained sample at the predetermined microwave frequency with a predetermined abosrption value at the same frequency for a contained sample taken from a melt containing a proper amount of dopant to produce an ingot of a desired resistivity;
introducing an amount of dopant into the melt if the measured value is significantly less than the desired value; and
introducing an amount of semiconductor material into the melt if the measured value is significantly greater than the desired value, whereby the resistivity of each of a plurality of single-crystalline ingots is controlled to achieve substantial uniformity of resistivity among successively grown ingots.

7. An apparatus for controlling the resistivity of each of a plurality of single-crystalline ingots of desired size which may be successively grown from a melt, which melt may be successively reconstituted as desired for each ingot grown, wherein the melt contains polycrystalline material and an impurity, and wherein the improvement comprises:
means for maintaining at least a portion of the melt in its melted state for each ingot grown from the melt which portion of melt may be retained and reconstituted for a successive ingot after an ingot is grown;
means for withdrawing a sample of the maintained melt, the composition of the melt varying as a single-crystalline ingot is grown from the melt and varying in accordance with the freezing of the melt into an ingot;
means for cooling the sample to solidify it into a polycrystalline structure;
means for determining an electrical characteristic of the polycrystalline sample which characteristic is indicative of the level of the impurity in the maintained melt and which level of the impurity in the maintained melt is indicative of the resistivity of a single-crystalline ingot grown from the melt;
means for comparing the determined electrical characteristic of the sample with a value of that electrical characteristic desired in an ingot; and
means for reconstituting the maintained melt according to the comparison and according to the desired size of an ingot by adding an amount of polycrystalline material or of the impurity or of both to the maintained melt to control the resistivity of each of a plurality of single-crystalline ingots grown from the melt.

8. An apparatus as recited in claim 7, wherein the means for withdrawing the sample is a hollow quartz member connected to a partial vacuum source and has a hollow rectangular portion for containing the sample of the polycrystalline melt, and wherein the determining means includes a slot adapted in size to receive the rectangular portion of the quartz member with the polycrystalline sample contained therein.

* * * * *